United States Patent [19]

Doran

[11] Patent Number: 4,670,256

[45] Date of Patent: Jun. 2, 1987

[54] VAGINAL CONDITIONING FOR SEXUAL ACTIVITY

[75] Inventor: Denny F. Doran, Lutz, Fla.

[73] Assignee: V. Valhalla Corp., Tampa, Fla.

[21] Appl. No.: 779,019

[22] Filed: Sep. 23, 1985

[51] Int. Cl.⁴ .................. A01N 63/00; A61K 37/00; A61K 9/40

[52] U.S. Cl. ............... 424/93; 424/DIG. 14; 424/433; 604/55; 604/288; 514/843; 514/967

[58] Field of Search ............... 514/967, 843; 424/DIG. 14, 37, 14, 16, 93; 604/55, 288

[56] References Cited

U.S. PATENT DOCUMENTS

| | | | |
|---|---|---|---|
| 3,091,241 | 5/1963 | Kellett | 424/28 |
| 3,358,687 | 12/1967 | Miley et al. | 604/288 |
| 3,639,566 | 2/1972 | Naito et al. | 424/14 |
| 3,875,013 | 4/1975 | Manautou et al. | 435/18 |
| 3,876,757 | 4/1975 | Scherm | 424/44 |
| 3,968,011 | 7/1976 | Manautou et al. | 435/18 |
| 3,997,459 | 12/1976 | Bogie et al. | 252/99 |
| 4,308,867 | 1/1982 | Roseman et al. | 424/16 |
| 4,384,003 | 5/1983 | Kazmiroski et al. | 514/967 |
| 4,417,993 | 11/1983 | Gergely | 424/53 |
| 4,425,332 | 1/1984 | James | 424/37 |
| 4,552,751 | 11/1985 | Inaba et al. | 424/16 |
| 4,585,651 | 4/1986 | Beck et al. | 424/89 |
| 4,585,792 | 4/1986 | Jacob et al. | 514/967 |

FOREIGN PATENT DOCUMENTS

| | | | |
|---|---|---|---|
| WO84/4675 | 12/1984 | World Int. Prop. O. | 514/967 |
| 2004462 | 4/1979 | United Kingdom | 514/967 |

*Primary Examiner*—Ronald W. Griffin
*Attorney, Agent, or Firm*—Charles A. McClure

[57] ABSTRACT

Conditioning of the vaginal tract for sexual activity, by a method including adjusting and controlling its surface pH, with soluble means for accomplishing such conditioning. The specified conditioning favors increased duration of sexual intercourse, as is often desired, and is compatible here with such diverse goals as favoring or discouraging conception. Normally the human vagina is strongly acidic, which may render intercourse with some males unduly brief. Through this invention the vaginal pH is increased about several pH units, by applying thereto a capsule, tablet, or suppository containing an alkalizer, to be released upon dissolution, so that the surface of the vaginal tract nears and preferably reaches or somewhat exceeds a neutral pH of 7 for a desired period of time. Thereafter, the vagina is enabled to return to its normally acidic condition, or is preferably actively returned thereto by subsequent release of an acidifier from such topically applied means.

25 Claims, 10 Drawing Figures

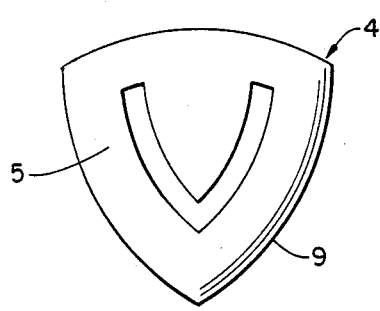
FIG. 4A
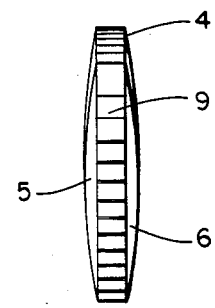
FIG. 4B
FIG. 5
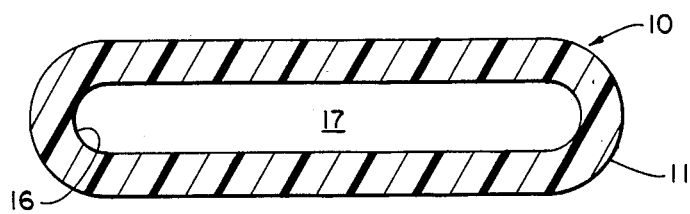
FIG. 6A 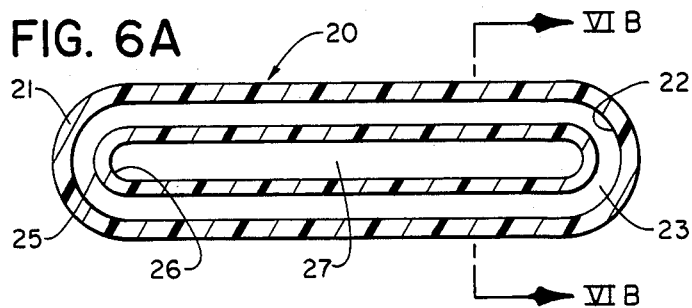 FIG. 6B 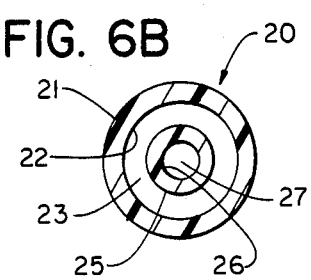

VAGINAL CONDITIONING FOR SEXUAL ACTIVITY

FIELD OF THE INVENTION

This invention relates to means and methods for conditioning the vaginal tract for sexual activity, especially by adjusting and controlling one or more surface physical-chemical characteristics (including pH specifically) over a desired period.

BACKGROUND OF THE INVENTION

A frequently expressed cause of dissatisfaction with human sexual intercourse is that it is so brief as to be disappointing rather than satisfying. It often is further frustrating in that it does not result in conception where that is desired. Although my perspective focuses principally upon human sexual activity, it is well known that failure of bred animals to conceive is a common source of disappointment for humans engaged in such a vocation. Hence, despite emphasis in this text upon human sexual activity, applicability of my invention to animal husbandry is also intended.

Although there may be many contributing reasons, emotional and psychological (presumably somewhat more in humans than in the lower animals) as well as physiological, for such undesired outcomes, my present invention considers undue brevity of intercourse in terms of certain physical-chemical conditions heretofore not very well appreciated in that regard.

Normally the surface condition of a healthy human vagina is acidic; it may even become somewhat more so during sexual activity. Yet an acid environment is known to be deleterious to the survival of spermatozoa. Indeed, if conception is not desired, more strongly acidic contraceptive compositions may be present intentionally at times of expected and actual sexual intercourse, which may further aggravate brevity thereof as a major cause of dissatisfaction.

Vaginal acidity also may curtail male participation in desired sexual activity, as in accelerating male orgasm, thus reducing the intended duration of sexual intercourse. Stronger acidity levels characteristic of some contraceptives can aggravate the difficulty.

Prior efforts to remedy such an unsatisfactory situation have tended toward reducing penile sensitivity, such as by interposition of a lubricated membrane or by topical application of one or another analgesic composition. Either method may prolong sexual engagement, but not usually very pleasurably for either the male or the female (and usually unfavorably for conception). Application of oils or other emollients directly to either the male or female organs may be helpful, but more as a palliative than as a solution to the problem.

Thus, a need exists for a better method of increasing the duration of sexual intercourse, where the duration is inadequate for reasons that can be treated purely physically. It would be desirable to be able to accomplish this regardless of whether a couple wish to conceive in doing so or wish to avoid conceiving, which would be their choice to make according to their own views. My invention provides just such a better method and also provides physical means especially designed for practicing it.

SUMMARY OF THE INVENTION

A primary object of the present invention is to condition the vaginal tract to favor penile contact of desirable duration.

Another object of this invention is to prolong future periods of sexual intercourse between partners with a history of rather brief periods thereof.

A further object of the invention is to enhance the ability to plan for and control the duration of desired sexual activity.

Yet another object is to provide compositions to accomplish such conditioning, together with carriers for such compositions.

A still further object of the invention is to accomplish the desired objects economically so as to be generally available.

In general the objects of the present invention are attained by compensating in novel manner for commonly encountered mistiming of biologically determined sexual reaction, and by novel means for implementing such compensation, whether in humans or other animals.

In particular this invention temporarily renders the vaginal tract non-acidic for a period of time wherein sexual activity is expected, such as up to several hours, after which it is restored to its normal acidity. Preferably the tract is rendered mildly alkaline initially, and then is rendered acidic after such lapse of time, all as a consequence of a user's single personal action.

Thus, a suppository, tablet, or the like is provided, for insertion into the vagina before contemplated sexual activity, to adjust and control vaginal pH as desired. Such a soluble device comprises a releasable alkaline constituent, and preferably a later releasable acidic constituent, well tolerated by the various bodily tissues to be contacted thereby. Timing is readily accomplished by providing for successive release of such constituents, embodying the diverse active components in gradually or successively soluble capsules, compartments, layers, mixtures, etc. Other compositions, such as surfactants, fragrances, emollients, and emulsifiers, or astringents, antiseptics, and the like, may be included therewith or may be introduced separately as desired.

Such methods and means for accomplishing the aforementioned and related objects of the invention will be apparent from the following description and the accompanying diagrams, which are presented by way of example rather than limitation.

BRIEF DESCRIPTION OF THE DRAWINGS

FIGS. 4A and 4B are front and side elevations of an embodiment of vaginal tablet according to the present invention;

FIG. 5 is a side sectional elevation of an embodiment of vaginal suppository useful according to this invention, FIGS. 6A and 6B axial and transverse sectional elevations through another embodiment of suppository according to the invention, having a plurality of compartments therein separated radially;

DETAILED DESCRIPTION

As noted above, the vaginal tract is normally rather acidic. According to the present invention such tract is rendered non-acidic temporarily. At the end of a given time duration, often a period of sexual activity, such as sexual intercourse, the tract is enabled to return to its normally acidic condition, as by natural secretion, or is restored promptly to such acidity, according to the invention.

Figure 1:
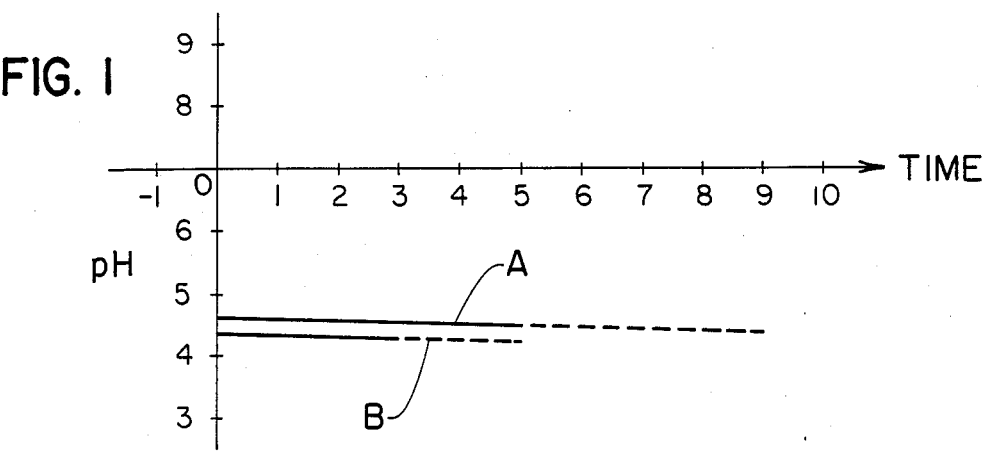
FIG. 1 is a pair of graphs indicating uncontrolled surface pH of the vaginal tract in terms of pH units (vertical scale) vs. time units (horizontal scale) of relatively long and relative short durations, respectively—such as of (or for) sexual activity.
Figure 2:
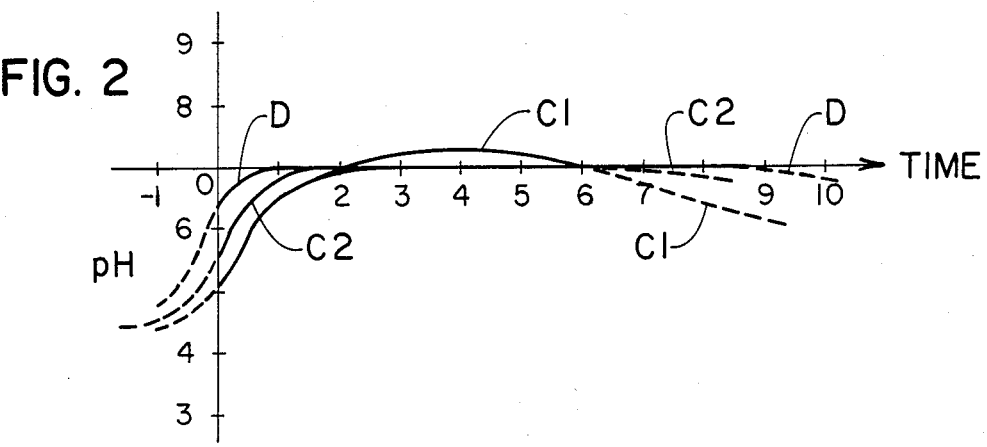
FIG. 2 is a trio of graphs of pH vs. duration, scaled like FIG. 1, of vaginal conditions variously controlled to neutral pH according to this invention over periods of similar duration.
Figure 3:
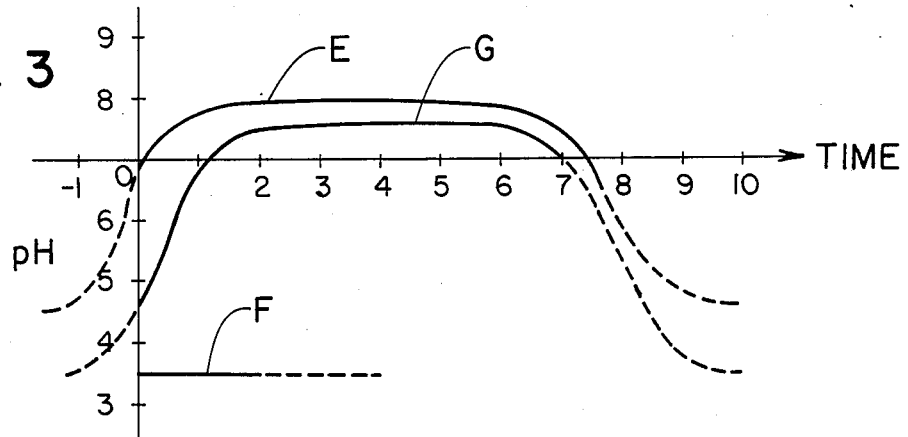
FIG. 3 is another trio of graphs of pH vs. duration, scaled like the preceding Figures, one of very acidic vaginal conditions without the benefit of the present invention, and two of initially alkaline—and then acidic—conditions according to the invention.

FIGS. 1 to 3 graph vaginal alkalinity or acidity conveniently in terms of pH on an ordinate scale centered at 7 (neutral) and extending downward to a pH of 3 (very acidic) and extending upward to a pH of 9 (mildly alkaline), vs. activity duration on an abscissa (scaled 1 to 10) in undesignated time units—which may be any suitably graduated number of minutes (such as 100, 200, or even more). As technically defined, pH is the logarithm of the reciprocal of the hydrogen ion concentration—or the negative logarithm of the same concentration. At the left of the vertical axis, the end portions of some of the curves (in broken lines) begin at times before the onset (time 0) of the period of defined duration, corresponding to administration of materials of this invention in contemplation of sexual activity. The right end portions of the curves appear in broken lines to indicate durations within that range on the time scale. The curves of these Figures are described first, and the methods and means whereby the examples of this invention are brought about are specified after intervening description of some physical embodiments of the invention.

FIG. 1 illustrates two diverse uncontrolled examples:
(A) normal conditions with adequate duration, and
(B) undesirably brief duration but otherwise normal.

In the curve of Example A, the initial pH is about 4.6, and the final pH about 4.4, with a duration of about 5 to 9 time units (broken line portion) as an example of normal duration of sexual activity (including intercourse) adequate for a majority of sexual partners. The ending range midpoint of 7 time units approximates both the most frequent (or modal) duration and the average (or arithmetic mean) time—for such group.

In the curve B example, on the other hand, the pH values are similar, beginning at about 4.4 and ending at about 4.3, but such ending occurs after a duration of only 3 to 5 time units, or an average of 4 units, which is deemed inadequate by most partners in comparison with A. Curve B, therefore, represents a kind of lack or need addressed by this invention.

FIG. 2 illustrates two examples of this invention wherein the pH is adjusted initially to essentially neutral and ultimately is enabled to return gradually to a more normal acidic condition:
(C1) an improvement upon Example B of FIG. 1 obtained by application of an unbuffered alkalizer;
(C2) a variant of Example C1, obtained by application of a buffered alkalizer;
(D) a further neutralizing variant, obtained via a mixture of an acid-soluble alkalizer and an acid-restoring composition.

In Example C1 FIG. 2, the pH curve rises gradually from a mildly acidic pH of about 4.3 to a neutral pH of 7 and overshoots somewhat to a maximum pH of about 7.5, then gradually diminishes and terminates below a neutral pH after about 6 to 8 time units. This action amounts to a gradual neutralization of the normally acidic condition in the vagina by a mildly alkaline composition, which establishes a mildly alkaline condition there temporarily. Thereafter, the natural vaginal secretions gradually neutralize the surplus alkalinity and restore the normally acidic condition.

In Example C2, in contrast to C1, the curve rises steeply from a like beginning at about a 4.3 pH to an essentially neutral pH of 7, where (being buffered) it remains for some half dozen time units and then (broken line) for a similar reason gradually trails off to slightly acidic lower pH readings to end after 6 to 8 time units.

The curve of Example D, representing in effect a dissolution and neutralization of an acid-soluble alkalizing composition, rises (as the normally acidic secretions react with it) to neutrality, and remains there for nearly the full scale of time as it continues to react with and neutralize any further acid secretions as produced. Upon exhaustion of the alkalizer, the pH trends slowly downward into increasingly acidic conditions to end at a pH near 6. This action is mentioned further in a later section on compositions.

FIG. 3 illustrates a more alkaline alternative to the previous examples, along with examples of undesirably short and satisfactorily long durations in very acidic starting and ending conditions:
(E) further compensation for unsatisfactory curve B by a sequential combination of buffered alkalizer and acidifier;
(F) brief duration in even more strongly acidic conditions than in B;
(G) compensation for F according to this invention.

The curve of Example E, in contrast to the preceding more neutral maxima, rises to a mildly alkaline pH just under 8, staying there for about a half dozen time units, and then drops abruptly to level out at about 4.5 on the broken line portion of the curve between 7 and 10 time units. Its average duration of at least about 8 time units matches or exceeds the normal A duration and satisfactorily doubles the (unsatisfactory) average B duration.

Curve F of FIG. 3 is characteristic of modification of the B situation by presence of an acidic contraceptive composition. It begins at a strongly acidic pH of about 3.5, and ends there after a duration of only several time units—within the broken line from 2 to 4 units. Such a brief duration is obviously at least as unsatisfactory as was the B duration.

Remedial Example G, as compared with F, shows a curve that begins at an initial very acid pH and rises similarly to the E curve of this invention to about a 7.5 pH, and remains there for a handful of time units, then drops promptly through neutral readings and (at about 7 time units) more abruptly. It matches the A and E curves at about 4.5 pH and 8 time units, and levels out at about a pH of 3.5 at a time of 10 units. The midpoint of its broken terminal part at about 8 time units is comparable to that attained in E, notwithstanding that its very low final pH is compatible with presence of a strongly acidic contraceptive.

It will be understood that the illustrated curves are only exemplary and are not necessarily typical of any entire population, but represent conditions such as are exhibited by, on the one hand, some of those people who have no experience of relatively brief intercourse duration, and—on the other hand—others who do have such a problem, and additionally some of the latter under conditions compensated for according to this invention.

Compositions suitable for assuring the diverse pH values in the curves of FIGS. 2 and 3 are identified below after discussion of structural embodiments (in FIGS. 4 to 8) useful in providing such desired compositions. Administration of an alkalizing composition as a douche or, at the other extreme, in the form of a powder is possible, of course. However, such means and methods preclude important benefits of this invention, and the preferred vehicle for suitable compositions is in the form of an insertable solid object, such as a homogeneous tablet or a (usually) non-homogeneous device called a "suppository". Table I matches the Examples and Figures.

TABLE I

| Cross-References of Examples and Figures | | | | | | | |
|---|---|---|---|---|---|---|---|
| GRAPH FIG.: | 1 | 1 | 2 | 2 | 2 | 3 | 3 | 3 |
| EXAMPLE: | A | B | C1 | C2 | D | E | F | G |
| EMBODIMENT FIG.: | — | — | 5 | 5 | 4–8 | 5–8 | — | 5–8 |

FIGS. 4A and 4B show an acid-soluble tablet embodiment, and FIGS. 5 to 8 show (on an enlarged scale) suppository embodiments, of the invention. It will be understood that any of such physical embodiments may be provided in a non-soluble sheath, wrapper, or the like (not shown) from which it is extracted for insertion into the vagina, where body moisture and temperature act to dissolve it over a predetermined time period, as desired, and thus to release its constituents or contents.

FIGS. 4A and 4B depict solid tablet 4 of this invention in a curvilinear triangular form, viewed first toward front face 5 and then toward edge 9, the latter view also showing part of curved front face 5 and rear face 6. This tablet is compartment-free, as its constituents are distributed fairly homogeneously throughout. As already noted, the chemical compositions of this embodiment and all of the various other embodiments are considered below, after each of the illustrated physical embodiments has been described.

FIG. 5 shows in longitudinal section first suppository 10 according to this invention. This soluble article comprises an elongated thick-walled gelatinous capsule or envelope 11, with optional hollow core 16 often holding (when present) contents 17.

In Example C1, the envelope composition, and in Example C2 the contents, is/are alkaline so as to neutralize the vaginal tract upon contact. In Example D, the constituents or contents comprise not only an alkalizer for that same purpose, but also means suitable for restoring the naturally acidic condition of the tract—or aiding in its restoration—gradually over an extended period of time, as is explained below in discussing suitable compositions.

Although such acidic restoration is not strictly essential to the desired time duration of sexual activity, failure of the vagina to return to a normal acidity would render it unduly susceptible to growth of yeasts and other similarly undesirable infections that flourish in such an environment at high pH levels. This invention undertakes to preclude such conditions by enabling or positively ensuring vaginal acidity after the desired duration of activity.

In Examples E and G, using the first embodiment (FIG. 5) of suppository, the alkaline envelope dissolves to raise the pH to a mildly alkaline pH and eventually releases acidic contents 17 to restore the vaginal tract to normal acidity. However, other physical embodiments (described below) enable sequential release of diverse contents. Preferably the first released contents (rather than—or in addition to—the surrounding envelope itself) alkalize the surface of the vagina for a desired period of time, and thereafter second released contents (whether in solid, liquid, emulsion, or gel form) neutralize the previously released alkalizer remnant and provide an acidic surplus to restore the vaginal surface to a desirably low pH, approximating its original degree of acidity.

FIGS. 6A and 6B show, in longitudinal and transverse section, respectively, second embodiment 20 of such suppository according to this invention. It comprises elongated thin-walled soluble gelatinous envelope 21 surrounding smaller elongated gelatinous envelope 25, which is thicker-walled or less readily soluble (or both) than larger envelope 21. The respective envelopes are spaced apart by annulus 23 of alkaline liquid (preferably in emulsion or gel form), retained by inner wall 22 of the outer envelope. The alkaline liquid is released, in use, upon eventual dissolution of the outer envelope. Hollow core 26 of the inner envelope contains acidic contents 27 (optionally in liquid, gel or emulsion, or particulate solid form), which is released into the vagina upon dissolution of the inner envelope after a desired time. The time delay is readily determinable and is dependent upon the thickness of the envelope wall and its solubility, as well as the dissolution rate of the contents, which can be adjusted as needed.

Figure 7:
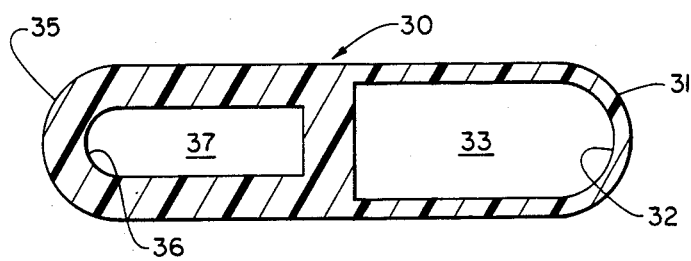
FIG. 7 is a side sectional elevation of yet another embodiment of vaginal suppository useful according to this invention, having a plurality of compartments therein separated transversely.

FIG. 7 shows, in longitudinal section, third embodiment 30 of a vaginal suppository according to this invention. Instead of being one inside the other as in the embodiment of FIGS. 5 and 6, here thin-walled readily soluble envelope 31 and thick-walled and/or less readily soluble envelope 35 form right and left end halves of an integrally formed elongated envelope structure outwardly similar to those illustrated in previous diagrams but divided into such pair of envelopes by transverse partition wall 34. Flat base portions of the respective envelopes in FIG. 7 are contiguous, intermediate the ends of the structure. Hollow core 32 of first envelope 31 contains alkaline liquid 33, which is released first into the vagina upon dissolution of that first envelope. Hollow core 36 of second envelope 35 contains acidic liquid 37, released considerably later by reason of the slower dissolution of the second envelope and the intervening partition.

Figure 8:
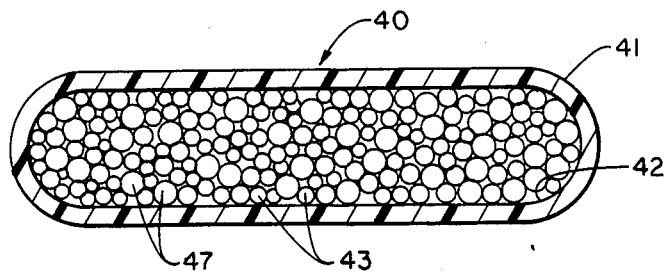
FIG. 8 is a side sectional elevation of a further embodiment of vaginal suppository useful according to the invention, having a multiplicity of individual beadlike elements in a compartment therein.

FIG. 8 shows in longitudinal section fourth embodiment 40 of suppository, being a modification of those shown previously. Here, elongated thin-walled soluble envelope 41 encloses in its hollow core 42 a multiplicity of beadlike capsules, shown in diverse sizes for the sake of clarity, including at least two types: more readily soluble beads 43 (shown small) comprising alkaline composition, and less readily soluble beads 47 (shown large) comprising acidic composition.

In size, tablet 4 measures about one to several centimeters on a side and from several millimeters to about a centimeter thick, and the various embodiments of suppository range from about one to a few centimeters in length, and from a few millimeters or so to a couple centimeters in diameter, depending upon the desired duration of activity and upon the dosage of the contained compositions—and whether such contents are solid or liquid and in what concentration.

The soluble material for the suppository wall(s) may be made of innocuous (even edible) material such as cocoa butter, gelatin, or methyl (or carboxymethy) cellulose, for example, with or without addition of other components, such as physical and/or chemical stabilizers, as are well known to minimize effects of unduly high or low temperature, for example. In a suppository embodiment wherein the suppository wall itself is neutralizing it conveniently comprises carboxymethyl cellulose cross-linked to trimethylolaminomethane and/or to triethanolamine. Otherwise, a suppository itself may comprise a neutral gel thereof or of gelatin or cocoa butter, as an envelope enclosing a neutralizing or alkalizing (or acidifying) composition, as the case may be. A solid tablet may mix together its constituent pH-adjusting materials along with an appropriate binder of starch, lactose, etc. with or without a gelatinous coating.

Compositions contained within and being released from a device of this invention to adjust and control vaginal pH are innocuous, numerous, and readily available. Examples include weak acids, such as acetic, boric, citric, and lactic; weak bases, such as ammonium, calcium, and magnesium hydroxides, and alkyl and aryl (and mixed) amines; salts of weak acids and bases, such as ammonium acetate and calcium carbonate, salts of strong bases and weak acids, such as sodium citrate and trisodium phosphate; and salts of weak bases and strong acids, such as ammonium or aluminum nitrate or sulfate, for example. Others will come to the mind of persons skilled in the art.

Alkaline envelope compositions for Example C1 have been noted. The curve illustrated for Example C2 is for the preferred hollow form in which the contents are compositions effective as a neutral (pH=7) buffer. An example utilizes 100 parts of monopotassium phosphate to 60 parts of sodium hydroxide. An alternative neutral buffering composition for C2 consists of 100 parts of disodium phosphate to 43 parts of citric acid, for example.

The constituent alkalizer(s) of tablet 4 in Example D of FIG. 2 are less readily soluble but are reactive with vaginal acid as long as such acid is present; for example, a mixture of calcium and magnesium hydroxides. An alternative composition comprises calcium carbonate, with or without such hydroxide(s). A composition also useful in Example D comprises live lactobacilli acidophilus such as Doerderleini, in suitable starch or equivalent nutrient, much as disclosed by Ibaraga in U.S. Pat. No. 3,639,566. Gradual growth of the lactobacillus occurs and progressively lowers the pH below an initial neutral level.

Other pH-adjusting compositions are more appropriate for the later examples. For Example E, the alkalizing component, in physical embodiments other than those already specified, conveniently comprises a buffering aqueous mixture of 100 parts monopotassium phosphate to 90 parts of sodium hydroxide at one to several tenths molar. Alternatives include like mixtures of 100 parts of of boric acid with 5 parts of sodium hydroxide or 100 parts of disodium phosphate plus 9 parts of citric acid. Concentration and/or quantity, as well as composition, are adjustable to compensate for actual vaginal extent and initial acidity level, as will be apparent to those skilled in the art.

The acidifying composition may, but need not, be buffered; it need only be capable of neutralizing all the known residual alkalizing component, with enough left over to enable the pH to approach a desired level, such as the starting levels indicated in curves E and G of FIG. 3. Suitable buffered acidifiers comprise 100 parts of potassium acid phthalate (i) to 20 parts of sodium hydroxide for Example E, or (ii) to 15 parts of hydrochloric acid for Example G. Alternative buffered mixtures include 100 parts of citric acid to 40 parts of disodium phosphate for Example E, or to 20 parts of disodium phosphate for Example G. Unbuffered aqueous citric acid can suffice for either example—in lesser amount for Example E than Example G will require. Other suitable alternative compositions and amounts will be apparent.

When conception is desired, release of the re-acidifying material may be further delayed by appropriate modification of its compartment wall, as by greater thickness or lesser solubility—or the acidifier may be omitted and be supplied separately. In Example G (FIG. 3) the alkalizing requirements are very similar to those of Example E except that the more acid initial condition may require more (if not more alkaline) alkalizing contents.

Also, in Example G, the acidifier, such as citric acid, may include zinc chloride as a spermicide—or alternatively for that purpose p-nonylpheloxypolyethoxyethanol or equivalent compound. Moreover, when conception is not desired, some other means, such as systemic chemical dosage (the "pill") or non-chemical method or means may replace or supplement such a topical spermicide.

A small quantity of malic acid may be utilized instead of (or in addition to) other acid to impart a pleasant scent to the composition generally. An emollient, such as glycerine, is also useful in maintaining adequate lubrication, especially if solid particulate material is present. A compatible antiseptic, such as boric acid, may be substituted as an acidifier, if desired.

Such a suppository is conveniently "finger-like" in form, with dimensions in ranges already noted. If the envelope wall is of a neutral composition, its volume should be subtracted in determining dosage; but not, of course, if it is alkalizing (or acidifying). The contained volume after total wall volume is deducted may well range from less than half the total volume to ninety percent or even more.

In practice, the total volume of a pH-adjusting device of this invention will depend upon the absolute quantity of the alkalizing or acidifying composition needed, upon whether such composition is in solid or liquid form, and upon its concentration (which in turn will depend upon any diluent present). Volume and concentration of compositions for accomplishing the objects of this invention are inversely related, of course, as a smaller but more concentrated volume of a given composition is essentially equivalent to a larger but more dilute volume thereof. Solid compositions, when used in other than tablet form, such as in a suppository envelope, are preferably in finely divided particulate form to aid dissolution. Any liquid content helps to maintain the vaginal tract desirably moist.

As little as 5 ml of liquid is capable of covering all or most of the vaginal surface to a depth of about a tenth of a mm, that is several thousandths of an inch, especially in the presence of a surfactant (such as sodium lauryl sulfonate) thereby rendering it satisfactorily moist even if solids must be dissolved. Recommended solids and aqueous or other liquid compositions should not harm the tissues contacted by them regardless of their concentration.

In the first described embodiment of suppository, its original shape and (in part) size will persist longer than in the instance of the other embodiments, as its thick wall is itself an alkalizer. Tablet embodiments usually will dissolve even more slowly. In the thin-walled suppository embodiments, part or all thereof dissolves much sooner, desirably before the onset of sexual intercourse, and thus releases the usually liquid contents (alternatively, small beadlike capsules in the fourth embodiment). Prompt dissolution of an outer envelope as in the second embodiment, or of an end compartment of a twin envelope as in the third embodiment, reduces the space occupied by the residue.

It will be understood that everyone (and, thus, every couple) is different and that human complexity reduces the predictability of behavior, especially sexual behavior, so that the foregoing examples are only emblematic of what may—not what must—occur. However, if the present invention benefits only a minor fraction of the possible candidates for its use it will have proved to be worthwhile. It also should prove similarly beneficial in animal husbandry, as when utilized to improve likelihood of conception.

The foregoing specification not only gives specific examples of the practice of this invention but also suggests variants or alternatives to aid readers in understanding the invention in its broad applicability. Other modifications may be made, as well, as by adding, combining, deleting, or subdividing parts or steps, while retaining at least some of the benefits of this invention, which itself is defined in the following claims.

I claim:

1. Method of conditioning a vaginal tract for a period of time suitable for sexual activity, comprising voluntarily administering thereto a material adapted to render the tract non-acidic for such period of time, and enabling it to become acidic at the end thereof.

2. Conditioning method according to claim 1, wherein the administered material includes a soluble composition adapted, upon dissolution, to render the tract non-acidic for such period of time.

3. Conditioning method according to claim 2, wherein the administered material comprises a solid mixture including an acid-soluble composition adapted to be dissolved and, in effect, titrated by acidic secretions in the vaginal tract.

4. Conditioning method according to claim 3, including in such mixture a quantity of lactobacilli acidophilus therefor, whereby growth thereof ensues and aids in rendering the tract acidic again.

5. Conditioning method according to claim 2, wherein the soluble composition includes an alkalizer, and including rendering the tract alkaline for at least part of such period.

6. Vaginal conditioning method according to claim 1, including embodying in a soluble envelope material for adjusting the vaginal pH in at least one preselected direction.

7. Method of conditioning a vaginal tract for a time period suitable for sexual activity, comprising selecting and administering thereto material adapted to render the tract non-acidic for such period of time, and further adapted to render the tract acidic thereafter.

8. Conditioning method according to claim 7, wherein the first material comprises a relatively readily soluble envelope surrounding an alkalizing composition, and the second material comprises a less readily soluble envelope surrounding an acidifying composition, whereupon the alkalizing composition is released upon dissolution of the readily soluble envelope at about the beginning, and the acidifying composition is released upon dissolution of the less readily soluble envelope at about the end, of such period.

9. Conditioning method according to claim 7, wherein the administered material includes an alkalizing composition and an acidifying composition, and including the steps of releasing alkalizing composition at the beginning of such period and releasing acidifying composition subsequently.

10. Conditioning method according to claim 9, wherein at least one such composition is soluble and is adapted, upon dissolution, to adjust the pH of the vaginal tract accordingly.

11. Conditioning method according to claim 9, including separately compartmenting the respective compositions in the administered material.

12. Method of conditioning a vaginal tract by application of pH-determining compositions thereto, comprising rendering it non-acidic initially and for a given period of time by topical application of a suitably buffered first composition thereto, and then rendering it acidic at the end of such period by application of a suitably acidic second composition thereto.

13. Conditioning method according to claim 12, wherein the first composition is characterized by a pH of about 7 to 9.

14. Conditioning method according to claim 12, wherein the first composition is acid-soluble and is naturally titrated by acidic secretions in the vaginal tract at a pH of about 7.

15. Vaginal conditioning method according to claim 12, including embodying in a first soluble envelope material for increasing the vaginal pH, and by embodying in an accompanying later soluble envelope material for reducing the vaginal pH.

16. Method of conditioning a vaginal tract, as for a time period suitable for sexual activity, comprising
arbitrarily selecting such a time period, and
theretofore increasing the pH of the tract, and
thereafter enabling it to decrease to normal acidity.

17. Vaginal conditioning method according to claim 16, wherein the pH is increased by topically applying alkalizing material to the tract.

18. Vaginal conditioning method according to claim 16, wherein the tract is passively enabled to return to normal acidity, including refraining from interfering with acidic bodily secretion in the vicinity.

19. Vaginal conditioning method according to claim 16, wherein the tract is actively enabled to return to normal acidity, including topically applying acidifying material thereto.

20. Vaginal conditioning method according to claim 16, including topically applying an alkalizing material to the tract at about the beginning of such a time period, and topically applying an acidifying material to the tract at about the end of such a time period.

21. Method of conditioning a vaginal tract, as for a time period suitable for sexual activity, comprising arbitrarily selecting such a time period, and initially raising the pH of the tract several pH units, and thereafter retunring it toward its original acidity.

22. Vaginal conditioning method according to claim 21, wherein the pH is increased to about 7, corresponding to approximate neutrality of the tract.

23. Vaginal conditioning method according to claim 21, wherein the tract is rendered mildly alkaline, corresponding to a pH fractionally above 7.

24. Vaginal conditioning method according to claim 21, including embodying in material for topical application to the vaginal tract at least one pH-adjusting composition so effective and releasing the same therein.

25. Vaginal conditioning method according to claim 24, including embodying in such material an alkalizer and a supply of lactobacilli acidopholus in nutrient medium, and including releasing alkalizer at about the beginning of the period of sexual activity and releasing the nutrient medium and supply of acidopholus lactobacillus at about the end of such period.

* * * * *